(12) United States Patent
Gorvel et al.

(10) Patent No.: US 9,061,066 B2
(45) Date of Patent: Jun. 23, 2015

(54) IMMUNOADJUVANT COMPOUNDS AND USES THEREOF

(75) Inventors: Jean-Pierre Gorvel, Marseilles (FR); Jacques Banchereau, Montclair, NJ (US); Anna Martirosyan, Marseilles (FR); Eynav Klechevsky, St. Louis, MO (US); Sangkon Oh, Dallas, TX (US)

(73) Assignees: Institut National de la Sante et de la Recherche Medicale (INSERM), Paris (FR); Centre National de la Recherche Scientifique (C.N.R.S.), Paris Cedex (FR); Universite d'Aix-Marseille, Marseilles (FR)

( * ) Notice: Subject to any disclaimer, the term of this patent is extended or adjusted under 35 U.S.C. 154(b) by 38 days.

(21) Appl. No.: 13/701,882

(22) PCT Filed: Jun. 6, 2011

(86) PCT No.: PCT/EP2011/059287
§ 371 (c)(1),
(2), (4) Date: Feb. 7, 2013

(87) PCT Pub. No.: WO2011/151471
PCT Pub. Date: Dec. 8, 2011

(65) Prior Publication Data
US 2013/0129756 A1    May 23, 2013

(30) Foreign Application Priority Data

Jun. 4, 2010    (EP) .................................... 10305596

(51) Int. Cl.
A61K 39/39    (2006.01)
A61K 39/00    (2006.01)
A61K 47/36    (2006.01)

(52) U.S. Cl.
CPC ................. *A61K 47/36* (2013.01); *A61K 39/39* (2013.01); *A61K 2039/55583* (2013.01)

(58) Field of Classification Search
None
See application file for complete search history.

(56) References Cited

U.S. PATENT DOCUMENTS 6,444,210 B1    9/2002  Kournikakis

OTHER PUBLICATIONS

Roset et al. J. Bacteriol. 188: 5003-5013, 2006.*
Hesagawa et al. Immunopharmacology 35: 273-282, 1997.*
Zwerdling et al., "*Brucella* lipoproteins mimic dendritic cell maturation induced by *Brucella abortus*", Microbes and Infection, Oct. 1, 2008, pp. 1346-1354, vol. 10, No. 12-13, Elsevier, Paris.
Briones et al., "*Brucella abortus* cyclic beta-1,2-glucan mutants have reduced virulence in mice and are defective in intracellular replication in HeLa cells", Infection and Immunity, Jul. 2001, pp. 4528-4535, vol. 69, No. 7.
Arellano-Reynoso et al., "Cyclic beta-1,2-glucan is a *Brucella* virulence factor required for intracellular survival". Nature Immunology, Jun. 2005, pp. 618-625, vol. 6, No. 6.

* cited by examiner

*Primary Examiner* — S. Devi
(74) *Attorney, Agent, or Firm* — Whitham Curtis Christofferson & Cook, PC (57) ABSTRACT

Cyclic beta glucan compounds function as an immunoadjuvant when administered prior to, concomitantly with, or subsequent to the administration of one or more antigens to a subject. These adjuvant compounds may be effectively used as dendritic cell activating molecules.

8 Claims, 6 Drawing Sheets

IMMUNOADJUVANT COMPOUNDS AND USES THEREOF

FIELD OF THE INVENTION

The present invention relates to a cyclic beta glucan compound for use as an immunoadjuvant and vaccine composition comprising thereof.

BACKGROUND OF THE INVENTION

The development of safe and efficacious vaccines remains a major goal in global public health.

The majority of the present day vaccines are composed of two main components: (i) the target antigen of therapeutic interest and (ii) immunoadjuvant(s) that stimulate and/or induce immunogenicity against said antigen.

The nature of known immunoadjuvants varies greatly, but includes in particular mineral oils, bacterial extracts, live and attenuated organisms and suspensions of aluminum hydroxide metals.

Even if immunoadjuvants provide enhanced immune responses, their use can also elicit adverse side effects, function notably of their administered route. Therefore, the numbers of immunoadjuvants that are approved and effective in humans remain relatively limited. Accordingly there is a need for new compounds which could be used as immunoadjuvants without triggering adverse side effects such as endotoxic side effect.

The immune response to bacterial infection relies on the combined action of both the innate and adaptive immune systems. Dendritic Cells (DCs) are the most efficient professional antigen-presenting cells APCs, which play an important role initiation and regulation of immune response. DCs are critical sentinels that detect, capture, and process antigens, such as invading bacteria and virus, and have the ability to migrate from peripheral tissues to secondary lymphoid organs to elicit primary T cell responses. Upon exposure to microbial stimuli, DCs undergo a maturation process characterized by the increased formation of MHC-peptide complexes, the up-regulation of co-stimulatory molecules (CD86, CD40 and CD80) and the cytokine production. Besides, other hallmarks of DC maturation process are the induction of chemokine receptors that facilitate movement into regional lymph nodes (CCR7) and the increase ability to activate T cells.

DCs recognize microbial stimuli, also called pathogen associated molecular patterns (PAMPs), by highly conserved receptors pattern-recognition receptors (PRRs). The best known and characterized classes of PRRs are the Toll-like receptors (TLRs) and C-type lectin receptors (CLRs). For example, lipoproteins and peptidoglycan are recognized by TLR2, dsRNA by TLR3, LPS by TLR4, CpG by TLR9, flagellin by TLR5, ssRNA by TLR7/8, CpG by TLR9, mannose-containing molecules by DC-SIGN and linear β-glucan by Dectin-1. When these receptors are triggered, downstream signalling cascades are activated for induction of inflammatory responses. Signalling pathways activated following TLR engagement can vary, depending on the recruitment or not of MyD88. MyD88-independent pathway that is unique to TLR3 and TLR4 leads to the expression of interferon regulatory factor 3 while MyD88-dependent signalling pathway, present on all TLRs except for TLR3, converge on MAPKs and NF-κB induction to exert their biological effects in fine.

Osmoregulated periplasmic glucans (OPGs) are general constituents of the periplasmic space of Gram-negative bacteria envelopes (22). They have been found in all the proteobacteria tested. OPGs exhibit quite different structures among various species but they share several common characteristics: (i) they are oligosaccharides made of a limited number of units (5 to 24); (ii) D-glucose is the only constituent sugar; (iii) glucose units are linked, at least partially, by β-glycosidic bonds; (iv) glucan concentration in the periplasm increases in response to a decrease of environmental osmolarity. OPGs seem to have a critical biological function because mutants deficient in OPG synthesis present highly pleiotropic phenotype (eg chemotaxis, motility, reduced outer membrane stability and synthesis of exopolysaccharides as well as defective growth in hypoosmotic media) (22). Besides, they are unable to establish successful pathogenic or symbiotic associations with eukaryotic hosts (1).

*Brucella* is a α-Proteobacteria considered as facultative intracellular pathogens of mammals, including humans. The pathogenesis of the resulting zoonosis, called brucellosis, is mostly linked to the ability of *Brucella* to survive and replicate intracellularly, in both professional and non-professional phagocytic host cells. In *Brucella* spp. cyclic beta glucans (CβG) consists of a cyclic backbone with a degree of polymerization ranging from 17 to 25, in which all the glucose units are linked by β-1,2 linkages (*Brucella* CβG) (2). It has been described that the presence of cyclic glucan is required for full *B. abortus* virulence (1). Moreover, Arellano-Reynoso et al. (3) determined that *Brucella* CβG, which modulates lipid microdomain organization, was essential for preventing lysosome fusion and allowing *Brucella* to reach its replicative niche. CβG are expressed in large amounts, representing 1-5% of the bacteria dry weight (ref). Therefore, considering that if the content of a single bacterium is released inside a *Brucella*-containing vacuole, the volume of which is about 10 femptoliter, the concentration of the CβG in the vacuole would be of a mM range. This means that when thousands of bacteria released from apoptotic cells die, CβG released in the external medium can be estimated in the µM range and this may have some important consequences on the immune system.

The role of glucans and especially linear beta glucans as important PAMPs involved in host-pathogen interactions (4, 5) has been extensively described. Interestingly, linear (1 - - - 3) β-glucans are recognized for their immunomodulatory properties, because they have been shown to possess antitumor (6) and anti-infective properties against bacterial (7), viral (8), fungal (9), and protozoal (10) infections. However, to date, there is no report about the properties of cyclic β-glucans as modulators of the immune system.

SUMMARY OF THE INVENTION

The inventors have been demonstrated that *Brucella* cyclic beta glucans (CβG) exhibit an immunoadjuvant activity as illustrated in the examples herein.

It has been also shown according to the present invention that these novel adjuvant compounds represent in particular a new class of dendritic cell activating molecules. The inventors for the first time demonstrate that *Brucella* CβG is a TLR4 agonist and a potent activator of mouse and human DCs since it is capable of inducing dendritic cell maturation, pro-inflammatory cytokine secretion and activation and proliferation of both CD4 and CD8 T cells.

Said new cyclic beta glucan compounds of the invention are thus particularly useful as immunoadjuvants, to induce and/or to enhance an immune response.

The present invention thus relates to an immunoadjuvant compound comprising at least one cyclic beta glucan compound.

The invention also relates to a vaccine composition comprising an immunoadjuvant compound as defined above, one or more antigens, and optionally one or more pharmaceutically acceptable excipients.

The present invention also relates to the immunoadjuvant compound as defined above, for use as a medicament (in particular to induce and/or to enhance adjuvant activity).

This invention also concerns the use of an immunoadjuvant compound according to the invention, for manufacturing a vaccine composition, in particular for inducing and/or for enhancing an immune response against one or more antigens.

The invention also relates to a kit containing:
an immunoadjuvant compound according to the invention, at least one antigen;
as combined preparation for simultaneous, separate or sequential use to induce a protective immune response against, for example, a pathogen, or to efficaciously protect the subject or the animal against infection.

A further object of the invention relates to a cyclic beta glucan compound for use in a therapeutic method for inducing maturation of dendritic cells (DCs) in a subject in need thereof.

Another further object of the invention relates to a cyclic beta glucan compound for use as immunoadjuvant, wherein said compound is use for inducing maturation of dendritic cells (DCs) in a subject in need thereof.

DETAILED DESCRIPTION OF THE INVENTION

The inventors have investigated the effect of *Brucella* cyclic beta glucans (CβG) and other cyclic glucans on DCs maturation, in term of production of cytokines, surface expression of MHC-II and co-stimulatory molecules, gene expression, toxicity and antibody responses on both human and mouse DCs. They have demonstrated that *Brucella* CβG are potent activators of mouse and human DCs. Furthermore, cyclic glucans with different structures did not induce the same activation responses, showing that CβG with different structures may have different activation properties. The inventors have also demonstrated that CβG represents a novel class of TLR4 agonists. It was indeed demonstrated that said cyclic beta glucan has a TLR4-mediated adjuvant properties, with in vivo pro-inflammatory effect, but do not shows any significant systemic endotoxic side effect after systemic injection. The results contained in the examples herein show that the said cyclic beta glucan does not show significant intrinsic antigenic effect, i.e. the molecule of interest prevents or attenuates the potency to trigger cyclic beta glucan antibodies, notably into serum. Accordingly, the inventors demonstrate that CβG could represent a next class of immunoadjuvant.

Accordingly, a first aspect of the invention relates to an immunoadjuvant compound comprising at least one cyclic beta glucan (CβG) compound.

The present invention also relates to a cyclic beta glucan compound for use as an immunoadjuvant.

As used herein, the term "immunoadjuvant" refers to a compound that can induce and/or enhance the immune response against an antigen when administered to a subject or an animal. It is also intended to mean a substance that acts generally to accelerate, prolong, or enhance the quality of specific immune responses to a specific antigen. In the context of the present invention, the term "immunoadjuvant" means a compound, which enhances both innate immune response by affecting the transient reaction of the innate immune response and the more long-lived effects of the adaptive immune response by activation and maturation of the antigen-presenting cells (APCs) especially Dentritic cells (DCs).

Accordingly a further object of the invention relates to a cyclic beta glucan compound for use in a therapeutic method for inducing maturation of dendritic cells (DCs) in a subject in need thereof.

Another further object of the invention relates to a cyclic beta glucan compound for use as immunoadjuvant, wherein said compound is use for inducing maturation of dendritic cells (DCs) in a subject in need thereof.

As used herein the term "antigen" refers to a molecule capable of being specifically bound by an antibody or by a T cell receptor (TCR) if processed and presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. An antigen can have one or more epitopes or antigenic sites (B- and T-epitopes).

As used herein, the term "cyclic beta glucan compound" or "CβG compound" refers to a low-molecular-weight cell surface carbohydrate with a cyclic backbone comprising between 17 and 25 hexose residues linked solely by beta-(1,2) glycosidic bonds. The hexose residues may be selected from the group consisting of naturally occurring hexose units and as well as structural alterations which incorporate non-naturally occurring hexoses, hexose analogs and mimetics. Those skills in the art know or can determine what structure constitutes functionally equivalent hexose analogs and hexose mimetics. Preferably, the naturally occurring hexose units may be selected from the group consisting of aldohexose which can form cyclic structure like allose, altrose, galactose, glucose, gulose, idose, mannose and talose. Preferably, naturally occurring hexose units are glucose.

In some embodiment various molecules can be attached to the cyclic beta glucan compound of the invention, covalently by using the free hydroxyle groups located on hexose units and/or non covalently by charge interactions created by the shape of the doughnut-like ring displaying a niche of about 10 A accepting molecules (11). The molecules may be selected from the group consisting of polypeptides, carbohydrates, nucleic acids or lipids (like cholesterol).

In some embodiments, the hexose residues may be substituted with at least one natural substituent residue. The "natural substituent residue" could means succinyl (Suc) residues (like in *Brucella abortus* CβG and *Sinorhizobium melitoti* CβG), phosphoglycerol residues (P-Gro) (like in *E. coli* CβG and *Sinorhizobium melitoti* CβG); phosphoethanolamine (P-Etn) residues (like in *E. coli* CβG);, phosphocholine residues (P-Cho) (like in *Bradyrhizobium japonicum* CβG);, acetyl (Ace) residues (like in *R. sphaeroides* CβG); methylmalonyl (MeMal) residues (like in *S. meliloti* CPG). In preferred embodiments, the natural substituent residue is succinyl residues. Such substitution occurs naturally in cyclic beta glucan of other bacterial species like *Brucella abortus* (O-succinyl residues). Other substitutions can be introduced in positions that do not alter the immunoadjuvant activity of the CβG. Typically, the substituent linkage on cyclic beta glucan compound is preferably made up of O-ester link on hydroxyl groups of the hexose. In some embodiments the number of natural substituent residue is comprise between, 0 to 25. In preferred embodiments the number of natural substituent residue is comprise between 0 to 3.

The skilled man in the art can evaluate easily the CβG compound having immunoadjuvant properties according to the invention by testing whether said compound induce maturation of dendritic cells by measuring cytokine production such as IL-12p and TNF-alpha production and expression of surface marker on dentritic cells such as CD80, CD40 and CD86. In second step, induction of CD8+T cell proliferation and activation can also be tested. Alternatively TLR4 agonistic activities may also be determined. Typically, the tests that may be used to test the immunodjuvant activity of a CβG compound are described in the Example.

The cyclic beta glucan compound of the invention may be obtained by purification of a bacterium, more preferably from *Brucella*, or by any one of the methods for chemical or oligosaccharides synthesis, that are well known from the one skilled in the art.

For example cyclic beta glucan compounds of interest may be recovered from culture medium or from bacterium cell lysates. Typically, the CβG compounds of the invention are isolated from *Brucella*. For example the CβG compound of the invention may be isolated from wild type *Brucella* cells or from *Brucella* strains such as *Brucella melitensis* 16M (American Type Culture Collection 23456; virulent strain, biotype 1), *Brucella abortus* 2308 (12). Bacterium employed in production of the cyclic beta glucan of interest can be disrupted by various physical or chemical means, such as freeze-thaw cycling, sonication, mechanical disruption, or cell-lysing agents.

It may be desired to purify the cyclic beta glucan of interest from bacteria. The procedures described in the Example are exemplary of suitable procedures for purification of CβGs from the supernatant of *Brucella melitensis* or *Brucella abortus*.

The following procedures are exemplary of suitable purification procedures of cyclic beta glucan compound: by fractionation on an ion-exchange column; ethanol precipitation (as used in the example); reverse phase HPLC; chromatography on silica or on a cation-exchange resin such as DEAE; chromatofocusing; SDS-PAGE; ammonium sulfate precipitation; gel filtration using, for example, SEPHADEX G-75; Protein A SEPHAROSE columns to remove contaminants; and metal chelating columns to bind epitope-tagged forms of the cyclic beta glucan of interest. Various methods of oligosaccharide purification may be employed and such methods like trichloracetic acid treatment and gel permeation chromatography are known in the art and described, for example, in (21).

The purification step(s) selected will depend, for example, on the nature of the production process used and the particular cyclic beta glucan compound produced.

Preparation and production of cyclic beta glucan compound, and specially with β-1,2 linkages, by cultivating a bacterium (*Agrobacterium* or *Rhizobium*), and collecting the titled compound from the culture solution are also described in JP 61040799 and JP61070994.

In certain embodiments, cyclic beta glucan compound of the invention may be synthesised through conventional techniques of chemical synthesis. For example international patent application WO 0216384 describes apparatus and methods for the automated synthesis of oligosaccharides for the efficient synthesis of oligosaccharides on a solid support, e.g., formed by subunit addition to terminal subunits immobilized on solid-phase particle. Cyclic beta glucan compound of the invention may also be synthesised by using the laminarinase 16A glycosynthase (23).

A further object of the invention relates to a vaccine composition, comprising a CβG compound according to the invention as an immunoadjuvant optionally with one or more pharmaceutically acceptable excipients. More particularly, the present invention pertains to a vaccine composition comprising an immunoadjuvant compound as defined above, together with one or more antigens.

A “vaccine composition”, once it has been administered to a subject or an animal, elicits a protective immune response against said one or more antigen(s) which is (are) comprised herein. Accordingly, the vaccine composition of the invention, once it has been administered to the subject or the animal, induces a protective immune response against, for example, a microorganism, or to efficaciously protect the subject or the animal against infection.

A variety of substances can be used as antigens in a compound or formulation, of immunogenic or vaccine type. For example, attenuated and inactivated viral and bacterial pathogens, purified macromolecules, polysaccharides, toxoids, recombinant antigens, organisms containing a foreign gene from a pathogen, synthetic peptides, polynucleic acids, antibodies and tumor cells can be used to prepare (i) an immunogenic composition useful to induce an immune response in a individual or (ii) a vaccine useful for treating a pathological condition.

Therefore, a cyclic beta glucan compound of the invention can be combined with a wide variety of antigens to produce a vaccine composition useful for inducing an immune response in an individual.

Those skilled in the art will be able to select an antigen appropriate for treating a particular pathological condition and will know how to determine whether an isolated antigen is favored in a particular vaccine formulation.

Those skilled in the art will be also able to determine whether it is preferable to covalently link, or not covalently link, the immunoadjuvant of the invention to the said one or more antigens. Thus, in a further aspect of the invention, the present invention relates to cyclic beta glucan compound according to the invention linked to at least one antigen.

An isolated antigen can be prepared using a variety of methods well known in the art. A gene encoding any immunogenic polypeptide can be isolated and cloned, for example, in bacterial, yeast, insect, reptile or mammalian cells using recombinant methods well known in the art and described, for example in Sambrook et al., Molecular cloning : A Laboratory Manual, Cold Spring Harbor Laboratory, New York (1992) and in Ansubel et al., Current Protocols in Molecular Biology, John Wiley and Sons, Baltimore, Md. (1998). A number of genes encoding surface antigens from viral, bacterial and protozoan pathogens have been successfully cloned, expressed and used as antigens for vaccine development. For example, the major surface antigen of hepatitis B virus, HbsAg, the P subunit of choleratoxin, the enterotoxin of *E. coli*, the circumsporozoite protein of the malaria parasite, and a glycoprotein membrane antigen from Epstein-Barr virus, as well as tumor cell antigens, have been expressed in various well known vector/host systems, purified and used in vaccines.

A pathologically aberrant cell may also be used in a vaccine composition according to the invention can be obtained from any source such as one or more individuals having a pathological condition or ex vivo or in vitro cultured cells obtained from one or more such individuals, including a specific individual to be treated with the resulting vaccine.

In a particular embodiment, the antigen of the vaccine composition could be a “Tumor associated antigen”. As used herein, the term “tumor associated antigen” refers to an antigen that is characteristic of a tumor tissue. An example of a tumor associated antigen expressed by a tumor tissue may be the antigen prostatic acid phosphatise (see WO 2004026238) or MART peptide T (melanoma antigen).

The vaccine composition according to the invention may contain at least one other immunoadjuvant. A variety of immunoadjuvant may be suitable to alter an immune response in an individual. The type of alteration desired will determine the type of immunoadjuvant selected to be combined with the said cyclic beta glucan compound of the invention. For example, to enhance the innate immune response, the vaccine composition of the invention can comprise another immunoadjuvant that promotes an innate immune response, such as other PAMP or conserved region known or suspected of inducing an innate immune response. A variety of PAMPs are known to stimulate the activities of different members of the toll-like family of receptors. Such PAMPs can be combined to stimulate a particular combination of toll-like receptors that induce a beneficial cytokine profile. For example, PAMPs can be combined to stimulate a cytokine profile that induces a Th1 or Th2 immune response. Other types of immunoadjuvant that promote humoral or cell-mediated immune responses can be combined with a cyclic beta glucan compound of the invention. For example, cytokines can be administered to alter the balance of Th1 and Th2 immune responses. Those skilled in the art will know how to determine the appropriate cytokines useful for obtaining a beneficial alteration in immune response for a particular pathological condition.

In another particular embodiment, the vaccine composition according to the invention, further comprises one or more components selected from the group consisting of surfactants, absorption promoters, water absorbing polymers, substances which inhibit enzymatic degradation, alcohols, organic solvents, oils, pH controlling agents, preservatives, osmotic pressure controlling agents, propellants, water and mixture thereof.

The vaccine composition according to the invention can further comprise a pharmaceutically acceptable carrier. The amount of the carrier will depend upon the amounts selected for the other ingredients, the desired concentration of the antigen, the selection of the administration route, oral or parenteral, etc. The carrier can be added to the vaccine at any convenient time. In the case of a lyophilised vaccine, the carrier can, for example, be added immediately prior to administration. Alternatively, the final product can be manufactured with the carrier.

Examples of appropriate carriers include, but are not limited to, sterile water, saline, buffers, phosphate-buffered saline, buffered sodium chloride, vegetable oils, Minimum Essential Medium (MEM), MEM with HEPES buffer, etc.

Optionally, the vaccine composition of the invention may contain conventional, secondary adjuvants in varying amounts depending on the adjuvant and the desired result. The customary amount ranges from about 0.02% to about 20% by weight, depending upon the other ingredients and desired effect. For the purpose of this invention, these adjuvants are identified herein as "secondary" merely to contrast with the above-described immunoadjuvant compound that is an essential ingredient in the vaccine composition for its effect in combination with an antigenic substance to significantly increase the humoral immune response to the antigenic substance. The secondary adjuvants are primarily included in the vaccine formulation as processing aids although certain adjuvants do possess immunologically enhancing properties to some extent and have a dual purpose.

Examples of suitable secondary adjuvants include, but are not limited to, stabilizers; emulsifiers; aluminum hydroxide; aluminum phosphate; pH adjusters such as sodium hydroxide, hydrochloric acid, etc.; surfactants such as Tween® 80 (polysorbate 80, commercially available from Sigma Chemical Co., St. Louis, Mo.); liposomes; iscom adjuvant; synthetic glycopeptides such as muramyl dipeptides; extenders such as dextran or dextran combinations, for example, with aluminum phosphate; carboxypolymethylene; bacterial cell walls such as mycobacterial cell wall extract; their derivatives such as *Corynebacterium parvum; Propionibacterium acne; Mycobacterium bovis*, for example, Bovine Calmette Guerin (BCG); vaccinia or animal poxvirus proteins; subviral particle adjuvants such as orbivirus; cholera toxin; N,N-dioctadecyl-N',N'-bis(2-hydroxyethyl)-propanediamine (pyridine); monophosphoryl lipid A; dimethyldioctadecylammonium bromide (DDA, commercially available from Kodak, Rochester, N.Y.); synthetics and mixtures thereof. Desirably, aluminum hydroxide is admixed with other secondary adjuvants or an immunoadjuvant such as Quil A.

Examples of suitable stabilizers include, but are not limited to, sucrose, gelatin, peptone, digested protein extracts such as NZ-Amine or NZ-Amine AS. Examples of emulsifiers include, but are not limited to, mineral oil, vegetable oil, peanut oil and other standard, metabolizable, nontoxic oils useful for injectables or intranasal vaccines compositions.

Conventional preservatives can be added to the vaccine composition in effective amounts ranging from about 0.0001% to about 0.1% by weight. Depending on the preservative employed in the formulation, amounts below or above this range may be useful. Typical preservatives include, for example, potassium sorbate, sodium metabisulfite, phenol, methyl paraben, propyl paraben, thimerosal, etc.

The vaccine composition of the invention can be formulated as a solution or suspension together with a pharmaceutically acceptable medium.

Such a pharmaceutically acceptable medium can be, for example, water, phosphate buffered saline, normal saline or other physiologically buffered saline, or other solvent or vehicle such as glycol, glycerol, and oil such as olive oil or an injectable organic ester. A pharmaceutically acceptable medium can also contain liposomes or micelles, and can contain immunostimulating complexes prepared by mixing polypeptide or peptide antigens with detergent and a glycoside, such as Quil A.

Liquid dosage forms for oral administration of the vaccine composition of the invention include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredient(s), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the vaccine compositions of the invention for rectal or vaginal administration may be presented as a suppository, which may be prepared by mixing the active ingredient(s) with one or more suitable non-irritating excipients or carriers comprising, for example, cocoa butter, polyethylene glycol, a suppository wax or salicylate and which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate Vaccine compositions of this invention suitable for parenteral administration comprise the active ingredient(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and non-aqueous carriers which may be employed in the vaccine compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly(orthoesters) and poly (anhydrides). Depot injectable formulations are also prepared by entrapping the active ingredient(s) in liposomes or microemulsions which are compatible with body tissue. The injectable materials can be sterilized for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The amount of antigen and immunoadjuvant compound in the vaccine composition according to the invention are determined by techniques well known to those skilled in the pharmaceutical art, taking into consideration such factors as the particular antigen, the age, sex, weight, species, and condition of the particular animal or patient, and the route of administration.

While the dosage of the vaccine composition depends notably upon the antigen, species of the host vaccinated or to be vaccinated, etc., the dosage of a pharmacologically effective amount of the vaccine composition will usually range from about 0.01 µg to about 500 µg (and in particular 50 µg to about 500 µg) of the immunoadjuvant compound of the invention per dose.

Although the amount of the particular antigenic substance in the combination will influence the amount of the immunoadjuvant compound according to the invention, necessary to improve the immune response, it is contemplated that the practitioner can easily adjust the effective dosage amount of the immunoadjuvant compound through routine tests to meet the particular circumstances.

The vaccine composition according to the invention can be tested in a variety of preclinical toxicological and safety studies well known in the art.

For example, such a vaccine composition can be evaluated in an animal model in which the antigen has been found to be immunogenic and that can be reproducibly immunized by the same route proposed for human clinical testing.

For example, the vaccine composition according to the invention can be tested, for example, by an approach set forth by the Center for Biologics Evaluation and Research/Food and Drug Administration and National Institute of Allergy and Infectious Diseases (13).

Those skilled in the art will know how to determine for a particular vaccine composition, the appropriate antigen payload, route of immunization, volume of dose, purity of antigen, and vaccination regimen useful to treat a particular pathological condition in a particular animal species.

In a vaccination protocol, the vaccine may be advantageously administered as a unique dose or preferably, several times e.g., twice, three or four times at week or month intervals, according to a prime/boost mode. The appropriate dosage depends upon various parameters.

As a general rule, the vaccine composition of the present invention is conveniently administered orally, parenterally (subcutaneously, intramuscularly, intravenously, intradermally or intraperitoneally), intrabuccally, intranasally, or transdermally, intralymphatically, intratumorally, intravesically, intraperitoneally and intracerebrally. The route of administration contemplated by the present invention will depend upon the antigen.

The present invention relates to a kit comprising an immunoadjuvant compound as defined above (i.e. a CβG compound according to the invention) and at least one antigen.

More particularly, the invention relates to a kit comprising:
an immunoadjuvant compound as defined above,
at least one antigen as defined above;
as combined preparation for simultaneous, separate or sequential use to induce a protective immune response against, for example, a pathogen, or to efficaciously protect the subject or the animal against infection.

A CβG compound can be administered prior to, concomitantly with, or subsequent to the administration of at least one antigen to a subject to induce a protective immune response against, for example, a pathogen, or to efficaciously protect the subject or the animal against infection. The CβG compound and the antigen are administered to a subject in a sequence and within a time interval such that the CβG compound can act together with the antigen to provide an increased immune response against said antigen than if they were administered otherwise. Preferably, the CβG compound and antigen are administered simultaneously to the subject. Also preferably, the molecules are administered simultaneously and every day to said patient.

A further aspect of the invention relates to a method for vaccinating a subject in need thereof comprising administering a pharmacologically effective amount of an antigen and a pharmacologically effective amount of an immunoadjuvant compound according to the invention As used herein, the term "subject" denotes a mammal, such as a rodent, a feline, a canine, and a primate. Preferably a subject according to the invention is a human.

A pharmacologically effective amount of the immunoadjuvant compound according to the invention may be given, for example orally, parenterally or otherwise, concurrently with, sequentially to or shortly after the administration of the antigen in order to potentiate, accelerate or extend the immunogenicity of the antigen.

The dosage of the vaccine composition will be dependent notably upon the selected antigen, the route of administration, species and other standard factors. It is contemplated that a person of ordinary skill in the art can easily and readily titrate the appropriate dosage for an immunogenic response for each antigen to achieve the effective immunizing amount and method of administration.

The present invention also relates to a TLR4 agonist, which consists of a CβG compound according to the invention.

As used herein, a TLR4 agonist refers to an agent that is capable of substantially inducing, promoting or enhancing TLR4 biological activity or TLR4 receptor activation or signalling.

A further object of the invention relates to a method for inducing the maturation of dentitic cells (DCs) in a subject in need thereof comprising administering a pharmacologically effective amount of an immunoadjuvant compound according to the invention.

The invention will be further illustrated by the following figures and examples. However, these examples and figures should not be interpreted in any way as limiting the scope of the present invention.

BRIEF DESCRIPTION OF THE FIGURES

A) Human monocyte-derived DCs were stimulated 24 h with media (neg), 10 ng/ml of *E. coli* LPS and 0.2 μM, 2 μM and 20 μM of *B. melitensis* CβG and HLA-DR, HLA-ABC, CD80, CD40, CD83 and CD86 surface levels were analyzed by FACS. B) Blood mDCs were stimulated with 20 mg/ml C13G for 24 h. Cytokines in the culture supernatants were measured by Luminex.

FIGS. 3A, 3B, and 3C. IL-12 production and CD80, CD40 and CD86 surface expression induced by *B. melitensis* CβG are dependent on TLR4.

DCs from WT (A, B and C), MyD88KO (A), TRIFKO (A), TLR2KO (B) and TLR4KO (B and C) mice were stimulated for 24 h with media (neg), CpG, PolyI:C, Pam2CSK4 and *B. melitensis* CβG. A and B) IL-12 concentration in culture supernatants was determined by ELISA. C) Surface levels of CD80, CD40 and CD86 were measured by flow cytometry. As positive controls: Pam2CSK4 (100 ng/ml), LPS (100 ng/ml), CpG (1 μM) and Poly I:C (1 mg/ml). Data are representative of three independent experiments. *p<0.05, compared to WT mice.

FIGS. 4A and 4B. Adjuvant activity of *B. abortus* CβG against venom of *Bothrops asper*.

A; The (**) in the mixture venom+calcium alginate+C13G indicate a value of p<0.001 with respect to the venom injected alone in a mixture of calcium alginate.

B. Adjuvant activity of C13G against the venom of Bothrops asper 21 days after immunization.Serum pools of 10 mice per group (total 30 mice). SD is less than 5%.

EXAMPLE 1

Bacterial β1,2 Cyclic Glucans Are Novel Dendritic Cell Activators

Materials And Methods

Antibodies And Reagents.

Fluorchrome-conjugated antibodies against CD8, CD45.2, CD44, CD25, and CD62L were purchased from BD Biosciences or eBiosciences.

Ovalbumine (OVA) was purchased from EndoGrade with purity>98% and endotoxin concentration <1 EU/mg.

Carboxyfluorescein diacetate succinimidyl ester (CFSE) was ordered from Invitrogen.

The Aqua Dead Cell Stain for 405 n excitation (Invitrogen) was used to detect dead cells for flow cytometry experiments.

SIINFEKL (SEQ ID NO 1) peptide was purchased from Schafer-N.

Cyclic Glucan Extraction, Purification And Characterization

Cyclic glucan molecules were obtained from *B. melitensis* 16M (American Type Culture Collection 23456; virulent strain, biotype 1), *Brucella abortus* 2308 (12) and Ralstonia solanacearum (purified CβG from *Ralstonia solanacearum* is a gift from Dr. J P Bohin, CNRS UMR8576, Lille, France). The strains were grown in a fermentor at 36° C. and 35% O2 saturation in a biosafety level 3 room in case of *Brucella* strains (14) and were inactivated with phenol (0.5% at 36° C. for 48 h). Bacteria were resuspended in distilled water (20 g wet weight in 100 ml) and were heated at 120° C. for 30 min. Cell debris was removed (8,000 g for 30 min at 4° C.) and the extract was precipitated with three volumes of ethanol at −20° C. overnight. The precipitate was removed (5,000 g for 10 min) and the supernatant was mixed with two volumes of ethanol. The new precipitate was collected (5,000 g for 10 min), was suspended in 175 mM NaCl, 0.05% NaN3 and 0.1 M Tris-HCl, pH 7.0, and was digested first for 18 h at 37° C. with nucleases (50 mg of DNase-II type V and RNase-A (Sigma-Aldrich) per ml) and then for 1 h at 55° C. followed by 24 h at 25° C. with proteinase K (50 mg/ml; Merck). The fluid was extracted for 30 min at 70° C. with a volume of phenol, then the mixture was chilled and centrifuged (8,000 g for 15 min at 0° C.) and the aqueous phase was collected and reextracted again with phenol using the same conditions. The waterphase was dialyzed, clarified by brief centrifugation and freeze-dried. The identity of cyclic glucan was confirmed by 13C-nuclear magnetic resonance spectroscopy, high-performance liquid chromatography and high-performance thin layer chromatography (TLC) as described by Aragon and co-workers. The absence of polysaccharides and lipopolysaccharides or other contaminants was demonstrated by ultraviolet spectrophotometry, SDS-PAGE, gel immunoprecipitation and 3-deoxy-D-manno-2-octulosonic acid determination (14).

Mice And Cells

HEK 293 cells were maintained in DMEM supplemented with 10% FCS.

Wild-type C57BL/6 mice and TLR2−/−, TLR4−/−, MyD88−/−−, TRIF−/− knockout (KO) mice were maintained at Centre d'Immunologie Marseille-Luminy (CIML), Marseille, France. Double (MyD88/TRIF−/−) KO cells were provided by Caetano Reis y Souza laboratory, London, UK.

Mouse bone marrow-derived DCs were prepared from 7-8 week-old female C57BL/6 mice or TLR2−/−, TLR4−/−, MyD88−/−, TRIF−/− knockout (KO) mice as previously described (15). Briefly, femurs and tibiae of mice were removed and freed of muscles and tendons. The bones were placed in 70% ethanol for 2 min and subsequently washed in PBS. Both bone ends were cut off, and the marrow was flushed out with RPMI 1640 medium. The cells were seeded in 24 well plates with complete RPMI 1640 (5% FCS and 50 μM β-mercaptoethanol) supplemented with mouse GM-CSF (mGM-CSF). On day 3, the media was change and on day 6 the experiment was carried out.

Mouse bone marrow-derived macrophages were prepared in the same way as bone marrow-derived DCs, from femurs of 7-8 week-old female C57BL/6 mice. Cells were seeds in complete DMEM (2 Mm L-glutamine, 10% FCS) supplemented with M-CSF. On day 5 and 6, media was changed and on day 7 the experiment was carried out.

Human monocyte-derived DCs were generated from FICOLL separated peripheral blood mononuclear cells (PBMCs) from healthy volunteers (16). Monocytes were enriched by adherence and were cultured in complete RPMI medium (supplemented with granulocyte-monocyte colony-stimulating factor (GM-CSF) and IL-4 during 6 days or GM-CSF and IFN during 3 days. Blood myeloid DCs (mDCs: HLA−DR+CD11c+CD123−Lin−) were sorted from PBMC using FACS aria (BD Biosciences, CA). Naive CD4+ and CD8+ T cells (CD45RA+CD45RO−) (purity>99.2%) were purified by FACS-sorting.

C57B1/6 Ly5.1 mice from Jackson Laboratory and OT-I TCR transgenic Ly5.2 mice on C57B1/6 background bred in CIML animal facilities were used for experiments.

Immunofluorescence Microscopy And Flow Cytometry

For immunofluorescence microscopy, stimulated DCs were fixed in 3% paraformaldehyde at 37° C. for 15 min and processed for immunofluorescence labelling as previously described (17).

Rabbit rivoli antibody against murine I-A (18) and mouse antibody FK2 (Biomol) were used as a primary antibodies. After staining, samples were either examined on a Leica DMRBE epifluorescencemicroscope or a Zeiss LSM 510 laser scanning confocal microscope for image acquisition. Images of 102431024 pixels were then assembled using Adobe Photoshop 7.0. Quantification was always done by counting at least 100 cells in 4 independent experiments, for a total of at least 400 host cells analysed.

For flow cytometry, stimulated DCs were collected and stained. FITC-conjugated antibody to CD80 and CD40, PE-conjugated antibody to CD83 and IA-IE (MHC class II) and APC-conjugated antibody to CD11c were obtained from Pharmingen. Appropiated isotype antibodies were used as controls. After staining, cells were washed with PBS and fixed in 3% of paraformaldehyde before analysis on a FAC-Scalibur cytometer (Becton Dickinson). Cells were always gated on CD11 c for analysis and 10,000 gated events were collected from each sample. The data was analysed using FlowJo software. Histograms were draw from and median fluorescence intensity values were determinated on gated population. To follow proliferation and activation of CFSE-labeled T cells, draining popliteal lymph nodes (DLNs) were collected 3 days after the immunization and subjected to collagenase type I digestion. Cells were stained for analysis by flow cytometry using different fluorchrome-conjugated antibodies. At least 100.000 events were collected on FACS-Canto II (BDBiosciences). Flow cytometry analysis was performed using FlowJo software.

Measurement of Cytokine Concentration

Total mouse IL-12 and TNF-alpha were quantified in culture supernatant of stimulated DCs by sandwich enzyme-linked immunosorbent assays (ELISA) according to the manufacturer's instruction (Abcys). Human cytokines and chemokines, including IL-1b, TNFa, and IL-12p40, were using the BeadLyte cytokine assay kit (Upstate, MA) as per the manufacturer's protocol.

Human CD4+ And CD8+ T Cell Responses $5 \times 10^3$ blood mDCs were co-cultured with CFSE-labeled allogeneic naïve CD4+ T cells ($1-2 \times 10^5$). Cell proliferation was tested by measuring CFSE-dilution on day 6. CD8+ T cells for 8-10 days in the presence of IL-2 (20 units/ml). $5 \times 10^3$ blood mDCs from HLA-A0201+ healthy donors were loaded with 0.2 m.o.i. (multiplicity of infection) heat-inactivated influenza virus (PR8) for 2 h at 37 oC. Autologous CD8+ T cells ($1-2 \times 10^5$) were mixed and cultured for 7 days in the presence of 20 units/ml IL-2. Cells were then stained with anti-CD8 antibody and tetramer (HLA-A*0201-Flu M158-66). MART-1-specific CD8+ T cell responses were measured after co-culturing with mDCs loaded with 10 mM MART-126-35 (27L) peptide.

Adoptive Transfer of OT-I T Cells And Immunization.

OT-I transgenic cells that express TCR specific for an H-2Db restricted CD8+ T cell epitope from OVA were used. Lymph nodes OT-I Ly5.2 mice were harvested and digested with collagenase type I (Sigma) at 37° C. for 30 min. CD8+ T cells were then negatively sorted by using mouse CD8 negative isolation kit (Dynal). Routinely, the resultant cells were >90%. CD8 percentage was determined by flow cytometry. CD8+ T cells were labeled with 10 μM CFSE at 37° C. for 10 min.

CD8+ Ly5.2 CFSE+ T cells were adoptively transferred intravenously (i.v.) into naive congenic C57B1/6 Ly5.1 recipient mice (200 000 cells/mouse). 24 h after OT-I adoptive transfer, recipient mice were immunized subcutaneously (s.c.) either with 30 μg OVA alone in endotoxin free PBS or 30 μg OVA mixed with 200 μg of cyclic glucan or 30 μg OVA mixed with 50 μg poly I/C or 30 μg OVA emulsified with IFA (volume/volume).

T Cell Proliferation And Activation.

Viable cells were always gated on CD8+CD45.2+ population and inventors analyzed the decrease of CFSE labeling which correlates with the cellular division. To study the cellular activation level, inventors looked at the expression of activation markers such as CD25, CD44 and CD62L.

HEK 293 Cells Luciferase Reporter Assay

HEK 293 cell reporter assays were performed as described previously ( ) using the indicated plasmids. Mouse TLRs, MD2 and CD14 cDNA were amplified by reverse transcriptase PCR from total RNA prepared from bone marrow-derived macrophages and subcloning in the pCDNA3.1 expression vector (Promega). HEK 293 cells were transiently tranfected using Fugene (Roche), according to manufacturer's instructions, for a total of 0.4 μg of DNA consisting of 50 ng of receptor plasmids, 200 ng of pBIIXLuc reporter plasmid, 5 ng of control Renilla luciferase (pRL-null, Promega).

After 24 h of transfection, cells were stimulated with described agonist for 6 h and then cells were lysed and luciferase activity measured using Dual-Glo Luciferase Assay System (Promega).

Results

*Brucella* CβG Is A Modulator of Mouse DC Maturation

Maturation of mouse DCs is characterized by many morphofunctional changes among them, the up-regulation of co-stimulatory and MHC class II molecules at the cell surface, change in morphology and the formation of large cytosolic dendritic cell aggresome-like induced structures, called DALIS, which are made of defective newly synthesised ubiquitinated proteins. To initially determinate whether *B. melitensis* CβG was an activator of the maturation of mouse DCs, cells were incubated with different concentration of *B. melitensis* CβG. After 8 and 24 h, surface expression MHC class II molecules and formation of DALIS were analyzed by confocal microscopy. As a control of DC activation, 0.25 mM of *E. coli* LPS were used. Mouse DCs treated with *B. melitensis* CβG or *E. coli* LPS, but not *Brucella* LPS underwent maturation, since they displayed MHC II surface localization and DALIS formation. However, in untreated DCs and DCs treated with *Brucella* LPS, MHC II molecules remained mostly intracellular and DALIS were not observed. the percentage of DCs with DALIS after incubation 8 h and 24 h with the respective stimuli. In the case of *E. coli* LPS, 80% of cells contained large and numerous DALIS after 8 h whereas only 20% of non-treated cells contained DALIS. *B. melitensis* CβG, at 0.025 μM already induced the formation of DALIS in 45% of the cells and at 0.25 μM and 2.5 μM the number of cells increased to 79% and 72%, respectively, reaching the levels obtained with 0.25 μM *E. coli* LPS. At 24 h, the number of DALIS started to decrease, which is consistent to what has been previously observed since DALIS expression in the process of DC maturation is transient event.

To obtain further insight into the effect of *B. melitensis* CβG in the DC maturation process, inventors next analyzed the surface expression of classical maturation markers (CD80, CD86, CD40 and MHC class II molecules) by flow cytometry in CD11c-positive mouse DCs. Analysis of the median of fluorescence showed a clear dose dependent induction of all co-stimulatory and MHC class II molecules by *B. melitensis* CβG. This is in agreement with microscopy observations where a high proportion of MHC class II molecules were present on cell surface.

These observations suggest that *B. melitensis* CβG promotes DC maturation. Inventors then investigated whether the secretion of cytokines by mouse DCs was also induced following *B. melitensis* CβG stimulation. The levels of IL-12 and TNF-alpha in the supernatants of stimulated mouse DCs were determined. Results showed that *B. melitensis* CβG induced the secretion of both cytokines in a dose dependent manner. This effect was observed at 8 h as well as at 24 h after stimulation, with no significant differences between both time points. Together, these data confirmed that *B. melitensis* CβG is a potent activating molecule of mouse DCs.

Mouse DC Maturation Is Modulated By Different Cyclic Glucan Structures

Inventors then investigated the possible relationship between cyclic glucan structure and DC activation by incubating DCs with various CβG from different origins. *B. melitensis* CβG consists of a cyclic backbone containing 17-25 glucose residues that are linked by β-1, 2 linkages (22). In the case of *B. abortus* CβG a fraction of the cyclic β-1, 2-glucans is substituted with O-succinyl residues (19). Ralstonia C13G is composed by a cyclic backbone with 13 glucoses. One linkage is α-1, 6 whereas all the other glucose residues are linked by β-1, 2 (22). The synthetic methyl-cyclodextrin (MβCD) consists of a 7 glucose cyclic backbone that are linked by β-1, 4-linkages and with O-methyl substitutions, which is also known for biologists as a lipid raft destructive agent using its property to extract membrane cholesterol (22).

First inventors analyzed the surface expression of maturation markers. *E. coli* LPS, *B. melitensis*, and *B. abortus* CβG induced a robust expression of CD80, CD86, CD40 and MHC class II molecules, although in slightly lower levels, were in cells incubated with *B. abortus* CβG. By contrast, *Ralstonia* CαG and MβCD failed to significantly activate DC.

Analysis of cytokines secretion corroborates surface marker expression. *B. melitensis* and *B. abortus* CβG induced TNF-alpha and IL-12 secretion. In response to *Ralstonia* CαG, DCs hardly produced TNF-alpha and IL-12 and in response to MβCD none of the cytokines were secreted.

The above data first demonstrated that cyclic glucan-dependent DC activation greatly depends on the molecule structure and secondly that cholesterol extraction does not have any effect on immune system responses in DC.

DC-Activation By CβG Requires TLR4, MyD88 And TRIF, But Is Independent of CD14.

We analysed the contribution of TLRs and adaptors for the recognition of CβG. MyD88 and TRIF are adaptor molecules involved in TLR signalling. MyD88 is involved in the TLR1, 2, 4, 5, 7, 8, 9, IL-1R and IL-18R pathways whereas TRIF is unique to TLR3 and TLR4. BMDC derived from TLR4, TLR2, MyD88, TRIF, TRIF/MyD88 and CD14 KO mice were treated with CβG. No activation could be observed in TLR4, Myd88, Myd88/TRIF and TRIF KO mice-derived BMDC stimulated either by *E. coli* LPS and *B. melitensis* CβG, as indicated by measuring surface expression of co-stimulatory molecules and secretion of pro-inflammatory cytokines such as IL-12, IL-6 and TNF-α (FIG. 2 And B). These results show that *B. melitensis* CβG induce DC maturation via the activation of the TLR4 pathway. To delineate the pathway involved in DC maturation induced by *B. melitensis*, CβG activation was tested in BMDC derived from MyD88KO, TRIFKO and double MyD88/TRIFKO mice. Similarly to *E. coli* LPS, the induction of IL-12 by *B. melitensis* CβG was hampered in BMDC derived from MyD88-KO and TRIF-KO mice, No IL-12 secretion was observed in double MyD88/TRIF KO when cells were incubated with *Brucella* CβG in contrast to DC treated with curdlan, a linear α-1,3 glucan from *Alcaligenes faecalis*. Curdlan is known to interact with the key β-glucan receptor Dectin-1 in a MyD88/TRIF-independent manner.

LPS recognition involves the LPS-binding protein (LBP), CD14 and the TLR4/MD2 complex. Secretion of pro-inflammatory cytokine such as IL-12 were completely abolished in *E. coli* LPS-treated CD14 KO BMDCs as well as cell surface expression of co-stimulatory molecules, MHC-II. In contrast, activation of CβG-treated BMDCs was independent of CD14. The fact that CβG does not require CD14 to activate the TLR4 pathway highlights a different mechanism of recognition than LPS. Altogether, these results demonstrate that CβG is a novel TLR4 agonist.

Potent biological inducers such as LPS display high toxicity and immunogenicity, properties that hamper the use of these molecules as adjuvant. It was therefore relevant to explore these properties in the purified *Brucella* CβG preparations. In contrast to *E. coli* LPS, *Brucella* CβG was not toxic for cell cultures or animals (Table 1) and did not induce the generation of antibodies in mice, rabbits or in naturally infected bovines (not shown). These results corroborate previous results showing that in cell culture, CβG was not toxic even at very high concentrations (10 mM). Thus, CβG is a TLR4 agonist that does not display the toxic properties of LPS.

Brucella CβG Induce A CD8 Response In Vivo.

Inventors investigated the ability of cyclic glucan to induce a CD8+ T cell response to an exogenous free antigen. Inventors transferred CD8+ Ly5.2 CFSE+ OT-I T cells into C57B1/6 Ly5.1 mice which were then immunized (s.c.) either with PBS alone (group 1), OVA alone (group 2), OVA with cyclic glucan (group 3) or OVA with known adjuvants such as Poly I/C (group 4) or IFA (group 5). Three days after the immunization inventors could observe an OT-I T cell proliferation in the draining lymph node in mice of all groups except the control immunized with PBS. We next explored the surface expression of activation markers in CD8+CD45.2+ population. Inventors analyzed by flow cytometry the up-regulation of CD25, CD44 expression and the down-regulation of CD62L, which correlates with T cells migration from lymph nodes to sites of infection. There was no cellular activation in mice vaccinated with PBS alone or PBS with OVA. However in the group immunized with OVA and cyclic glucan, inventors could observe a CD25 and CD44 up-regulation, as well as a strong down-regulation of CD62L expression, which is higher than in groups immunized with known adjuvants as Poly:IC.

These data indicate CβG can induce CD8+T cell proliferation and activation in vivo.

Brucella CβG Induce Maturation of Human DCs.

Figure 1A:
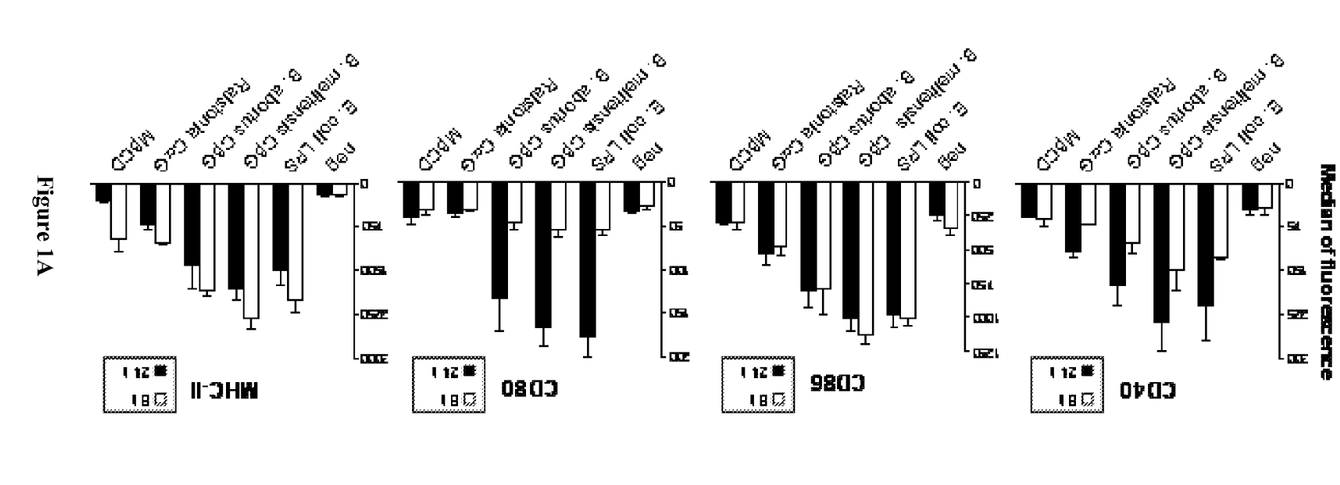
FIGS. 1A and 1B: Induction of mDC maturation depends on the structure of the cyclic glucan. Mouse DCs were stimulated for 8 h and 24 h with media (neg), *E. coli* LPS or *B. melitensis* C.βG, *B. abortus* CβG, *Ralstonia* CβG and MβCD at an equivalent concentration of 0.25 mM. Surface levels of MHC-II, CD80, CD40 and CD86 were measured by flow cytometry and IL-12 and TNF-alpha levels in culture supernatant were determined by ELISA (B). Data are representative of at least three independent experiments. *$p<0.05$ compared to negative.
Figure 1B:
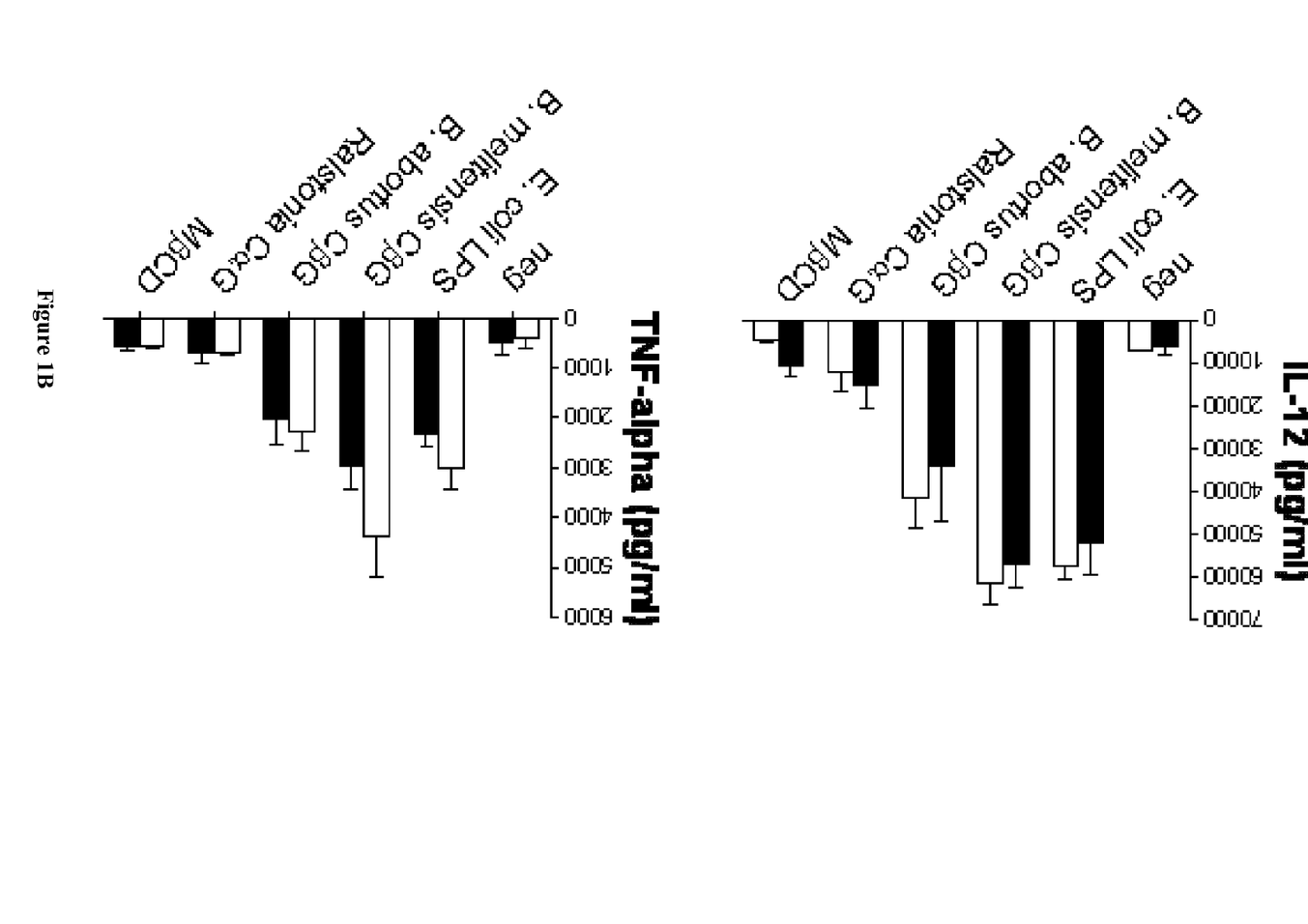
Figure 2A:
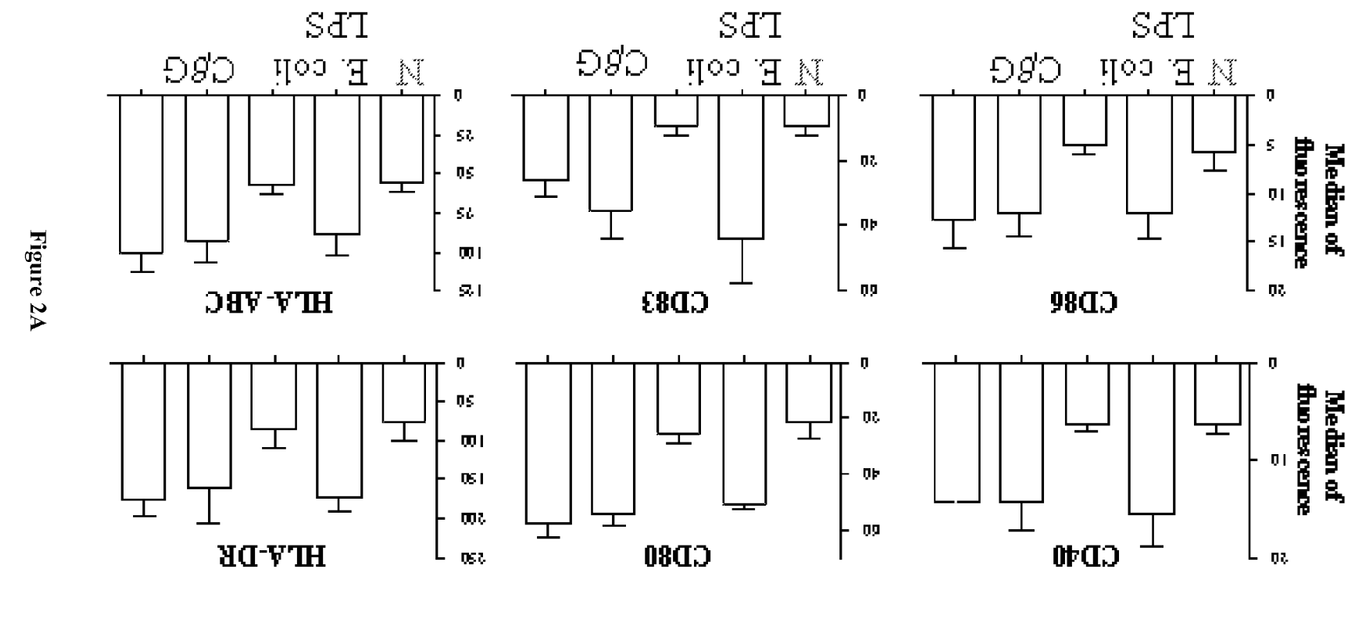
FIGS. 2A and 2B. *B. melitensis* CβG human DCs enhances CD4+ and CD8+ T cell responses.
Figure 2B:
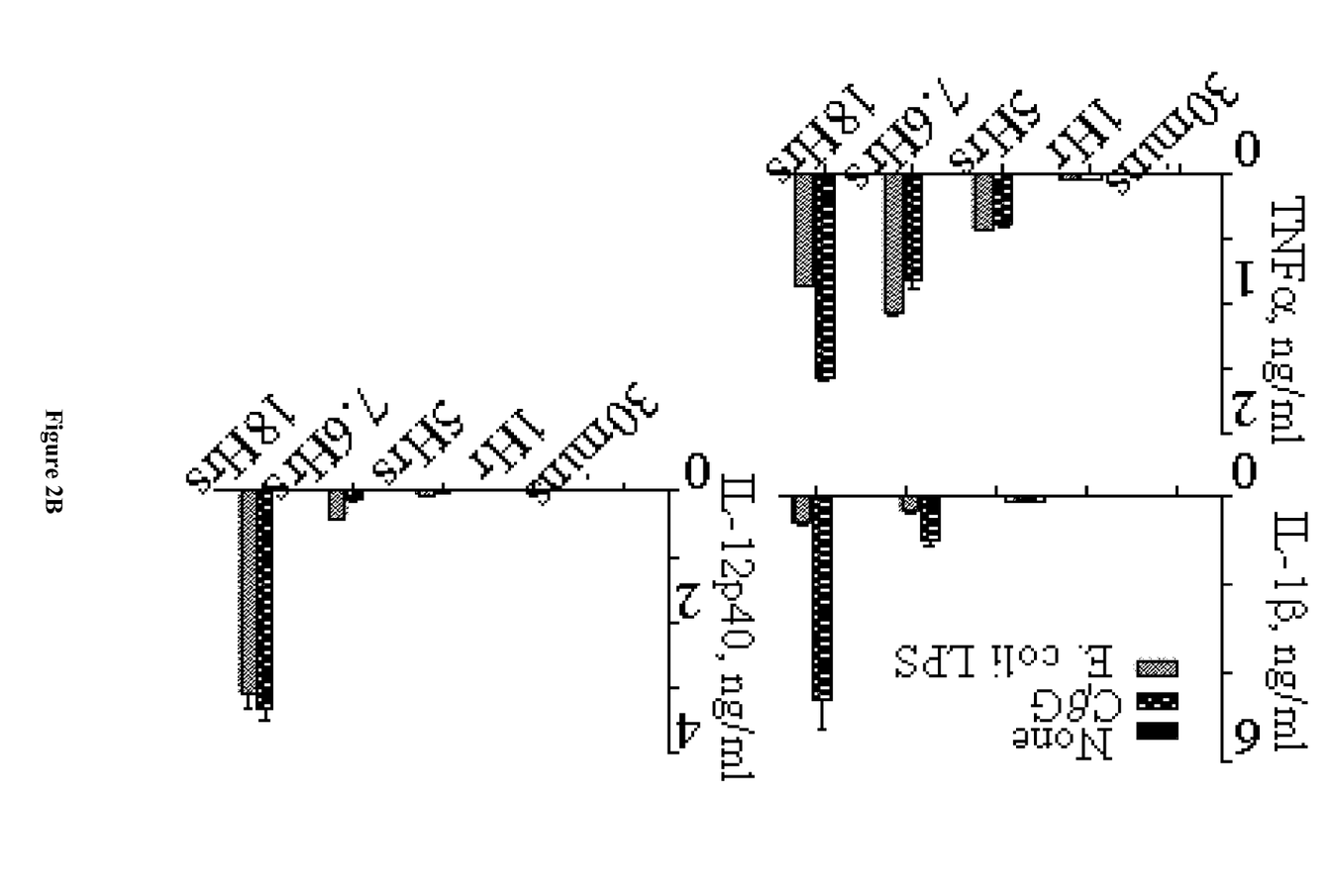
Figure 3:
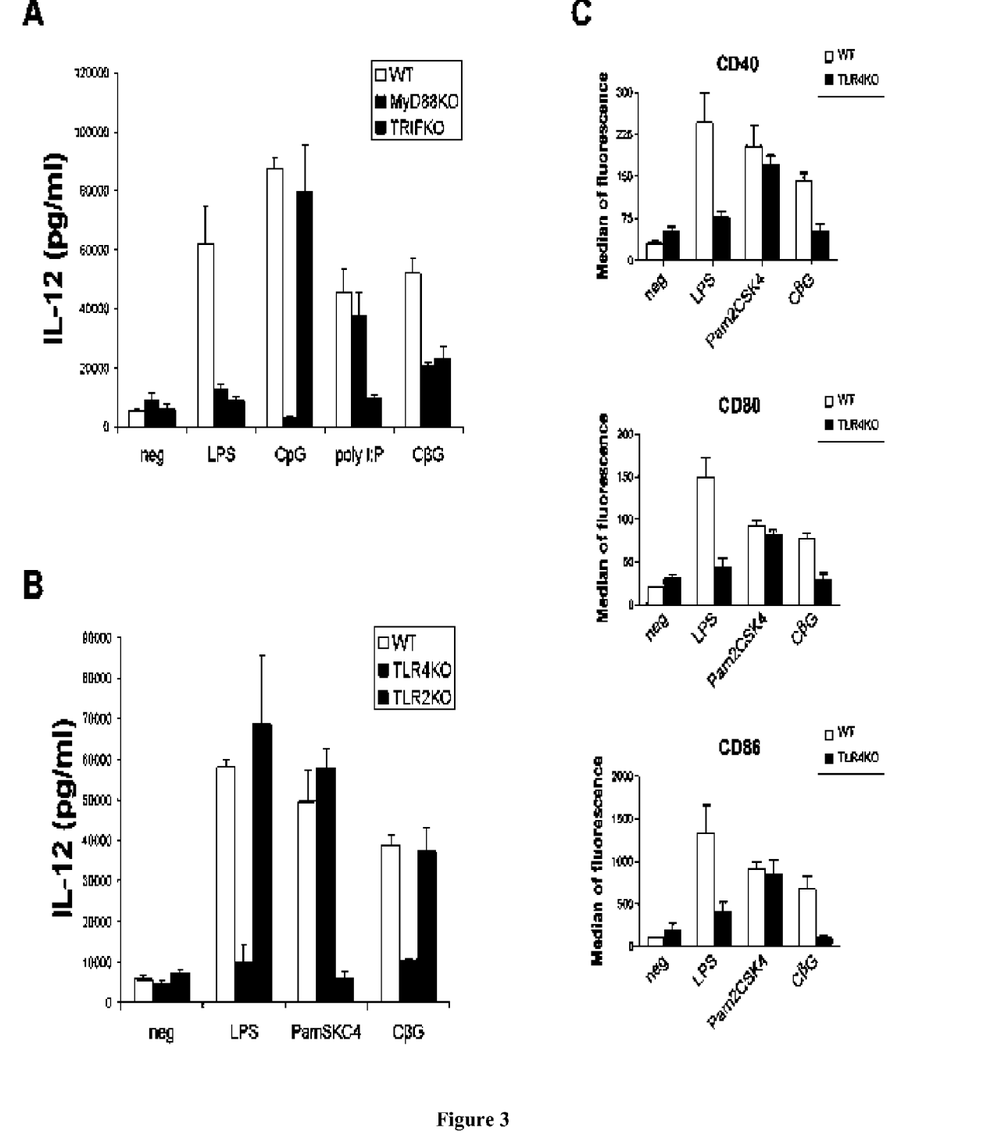

Inventors investigated whether B. melitensis CβG was also a stimulus for human monocyte-derived DC. Human DCs were differentiated from monocytes obtained from human peripheral blood in the presence of GM-CSF and IL-4 for 6 days or GM-CSF and IFN for 3 days. Inventors therefore tested the effect of various concentrations of B. melitensis CβG on DCs maturation. In IFN-differentiated DC, the up-regulation of CD80, CD83, CD40, HLA-DR, HLA-ABC and CD86 on the cell surface was detected in a dose dependent manner after treatment during 24 h with B. melitensis CβG (FIG. 2A). As in mouse DC, the lower concentration used (0.2 µM) was not able to induce this DC phenotype. The same result was present for IL-4-differentiated human DCs. Inventors further demonstrated that CβG efficiently activate human blood mDCs, resulting in significant amounts of IL-1b, TNFα, and IL-12, as observed in mouse DCs. In particular, CβG was more potent than E. coli LPS for the induction of IL-1b from blood mDCs (FIG. 2B).

mDCs activation with CβG resulted in increased allogeneic naïve CD4+ T cell proliferation. It also resulted in enhanced Flu M1-specific CD8+ T cell responses as well as MART-1specific CD8+ T cell responses. Although CβG was more efficient than E. coli LPS for CD4+ T cell proliferation, both CβG and E. coli LPS resulted in similar levels of Flu M1-specific CD8+ T cell responses as shown in the cross-presentation assay.

Taking together, these results indicated that Brucella CβG is a pan-activator of DC and macrophages.

Brucella CβG Is Not Endotoxic In Vivo And In Vitro.

Because CβG was able of triggering a strong activation and because it seemed that the mediated activation was dependent on the TLR4 pathway, inventors looked at the possible endotoxicity generated in vitro and in vivo. Different assays were used, in particular the Limulus amoebocyte lysate assay, the DL50 in Swiss mice injected by the various agonists and the toxicity in macrophages as measured by Chromium release.

Table I shows that CβG was not toxic at all compared to E. coli LPS and Brucella LPS. As expected, compared to Brucella LPS, E. coli LPS was able to induce an endotoxic shock at very low concentration.

TABLE I

B. melitensis CβG is devoid of endotoxic properties

| | Limulus amoebocyte lysate | LD50 in mice | Toxicity in macrophages |
|---|---|---|---|
| E. coli LPS | 0.1 ng/ml | 65 µg | 25 µg |
| B. melitensis LPS | 0.1 ng/ml | >250 µg | >50 µg |
| B. melitensis CβG | >105 ng/ml | >500 µg | >100 µg |

Limulus amoebocyte lysate from Pyrogent MA Bio products Inc. Walkersville USA. Method was performed according to the manual instruction.

LD50 was determined in Swiss mice (20 to 22 g), with 0.1 ml of the appropriate LPS concentrations. Deaths were recorded at 12, 24, 48 and 72 h, and the 50% lethal dose was determined by the probit method. The probit Method. (20). Toxicity for peritoneal macrophages was performed using the Chromium release method.

EXAMPLE 2

Adjuvant Activity of Brucella CβG

Methods

The adjuvant activity of CβG for induction of antibodies against snake venom was evaluated according to the method proposed by (24). Briefly, the venom of Bothrops asper diluted in PBS was mixed with calcium alginate or with PBS (control) and the mixture was emulsified. Then CD-1 mice were injected subcutaneously with the mixture, to give an equivalent to 20 µg of venom in a volume of 50 µl/mouse. Another group of mice was injected through the same route with the same mixture of calcium alginate and venom but also including 100 µg of B. abortus CβG per mouse. Finally a group of mice was only inject venom diluted in PBS. Immunized mice were bleed from the day "0" to day 30, and the antibody against the venom of B. asper were determined by indirect ELISA using plates coated with whole venom antigen and as conjugate anti-mouse Ig-horseradish peroxidase (24). The independent values of the different groups of mice were evaluated and the differences assessed by unidirectional ANOVA analysis, followed by Fisher significance (PLSD) analysis.

Results

Figure 4:
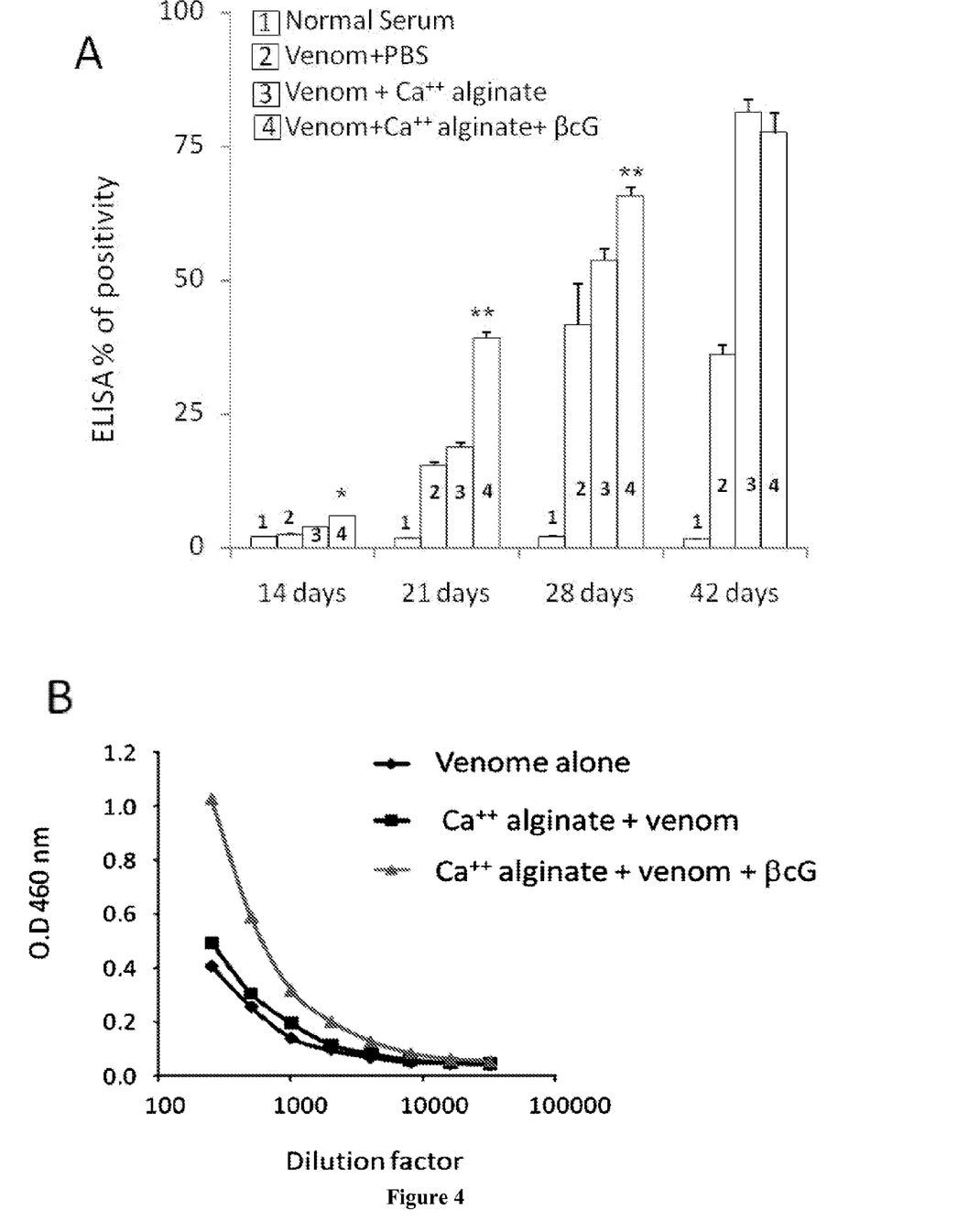

Calcium alginate is the immunoadjuvant classically used to induce an immunological response toward venom. As shown in FIG. 4 CβG synergizes with calcium alginate for the production of anti-venom immunoglobulins after 21 and 28 days (FIG. 4A). The kinetic of antibodies production is thus accelerated and the adjuvant activity is higher than the one observed with calcium alginate alone (FIG. 4B).

REFERENCES

Throughout this application, various references describe the state of the art to which this invention pertains. The disclosures of these references are hereby incorporated by reference into the present disclosure.

1. Briones, G. et al. *Brucella abortus* cyclic beta-1,2-glucan mutants have reduced virulence in mice and are defective in intracellular replication in HeLa cells. Infect. Immun. 69, 4528-4535 (2001).
2. Inon, d., I, Briones, G., Tolmasky, M. & Ugalde, R. A. Molecular cloning and characterization of cgs, the *Brucella abortus* cyclic beta(1-2) glucan synthetase gene: genetic complementation of *Rhizobium meliloti* ndvB and *Agrobacterium tumefaciens* chvB mutants. J. Bacteriol. 180, 4392-4400 (1998).
3. Arellano-Reynoso, B. et al. Cyclic beta-1,2-glucan is a *Brucella* virulence factor required for intracellular survival. Nat. Immunol. 6, 618-625 (2005).
4. Brown, G. D. & Gordon, S. Immune recognition of fungal beta-glucans. Cell Microbiol. 7, 471-479 (2005).
5. Netea, M. G. et al. Immune sensing of *Candida albicans* requires cooperative recognition of mannans and glucans by lectin and Toll-like receptors. J. Clin. Invest 116, 1642-1650 (2006).
6. Seljelid, R. A water-soluble aminated beta 1-3D-glucan derivative causes regression of solid tumors in mice. Biosci. Rep. 6, 845-851 (1986).
7. Kokoshis, P. L., Williams, D. L., Cook, J. A. & Di Luzio, N. R. Increased resistance to *Staphylococcus aureus* infection and enhancement in serum lysozyme activity by glucan. Science 199, 1340-1342 (1978).
8. Itoh, W. et al. Immunopharmacological study of sulfated schizophyllan (SPG). I.—Its action as a mitogen and anti-HIV agent. Int. J. Immunopharmacol. 12, 225-233 (1990).
9. Williams, D. L., Cook, J. A., Hoffmann, E. O. & Di Luzio, N. R. Protective effect of glucan in experimentally induced candidiasis. J. Reticuloendothel. Soc. 23, 479-490 (1978).
10. Cook, J. A., Holbrook, T. W. & Dougherty, W. J. Protective effect of glucan against visceral leishmaniasis in hamsters. Infect. Immun. 37, 1261-1269 (1982).
11. Mimura M, Kitamura S, Gotoh S, Takeo K, Urakawa H, Kajiwara KCarbohydr Res. 1996 Aug 19;289:25-37. Conformation of cyclic and linear (1-->2)-beta-D-glucans in aqueous solution.
12. Pizarro-Cerda, J. et al. *Brucella abortus* transits through the autophagic pathway and replicates in the endoplasmic reticulum of nonprofessional phagocytes. Infect. Immun. 66, 5711-5724 (1998).
13. Goldenthal, KL et al. AID Res Hum Retroviruses, 9: S45-9 (1993)
14. Aragon, V., Diaz, R., Moreno, E. & Moriyon, I. Characterization of *Brucella abortus* and *Brucella melitensis* native haptens as outer membrane O-type polysaccharides independent from the smooth lipopolysaccharide. J. Bacteriol. 178, 1070-1079 (1996).
15. Inaba, K. et al. Generation of large numbers of dendritic cells from mouse bone marrow cultures supplemented with granulocyte/macrophage colony-stimulating factor. J. Exp. Med. 176, 1693-1702 (1992).
16. Dhodapkar, K. M. et al. Selective blockade of inhibitory Fcgamma receptor enables human dendritic cell maturation with IL-12p70 production and immunity to antibody-coated tumor cells. Proc. Natl. Acad. Sci. U.S.A 102, 2910-2915 (2005).
17. Pizarro-Cerda, J. et al. *Brucella abortus* transits through the autophagic pathway and replicates in the endoplasmic reticulum of nonprofessional phagocytes. Infect. Immun. 66, 5711-5724 (1998).
18. Pierre, P. et al. Developmental regulation of MHC class II transport in mouse dendritic cells. Nature 388, 787-792 (1997).
19. Roset, M. S., Ciocchini, A. E., Ugalde, R. A. & Inon, d., I The *Brucella abortus* cyclic beta-1,2-glucan virulence factor is substituted with O-ester-linked succinyl residues. J. Bacteriol. 188, 5003-5013 (2006).
20. Haskell G., Science, 1950 111:43.
21. Talaga P, Cogez V, Wieruszeski JM, Stahl B, Lemoine J, Lippens G, Bohin J P. Osmoregulated periplasmic glucans of the free-living photosynthetic bacterium *Rhodobacter sphaeroides*. Eur J Biochem. 2002 May; 269 (10):2464-72.
22. Bohin, J. P. Osmoregulated periplasmic glucans in Proteobacteria. FEMS Microbiol. Lett. 186, 11-19 (2000).
23. Vasur J, Kawai R, Jonsson KH, Widmalm G, Engstrom A, Frank M, Andersson E, Hansson H, Forsberg Z, Igarashi K, Samejima M, Sandgren M, Ståhlberg J. Synthesis of cyclic beta-glucan using laminarinase 16A glycosynthase mutant from the basidiomycete *Phanerochaete chrysosporium*. J Am Chem Soc. 2010 Feb 10; 132 (5):1724-30.
24. Rucavado A, Moreno E, Gutiérrez J M. Effect of adjuvants on the antibody response of mice to *Bothrops asper* (Terciopelo) snake venom. Braz J Med Biol Res. 1996 October; 29 (10):1337-40.

The invention claimed is:

1. A method of enhancing an immune response against one or more isolated or purified antigens in a mammalian subject in need thereof comprising administering to the subject concomitantly with a pharmacologically effective amount of said one or more isolated or purified antigens and an adjuvant effective amount of an immunoadjuvant comprising at least one purified, isolated or synthesized cyclic beta glucan (CβG), wherein said at least one CβG stimulates the subject's immune system and induces dendritic cell activation and maturation in said subject, thereby enhancing said subject's immune response to said one or more isolated or purified antigens.

2. The method of claim 1 wherein said at least one CβG is substituted with at least one natural substituent residue.

3. The method of claim 2 wherein the at least one natural substituent residue is a succinyl residue.

4. The method of claim 2, wherein the at least one natural substituent residue includes a number of natural substituent residues which range between 0 to 25.

5. The method of claim 1, wherein the at least one CβG is a CβG obtained from *B. melitensis* and/or *Brucella abortus*.

6. The method of claim 4, wherein the number of natural substituent residues ranges between 0 to 3.

7. The method of claim 1, wherein said immune response includes both an adaptive immune response and an innate immune response.

8. The method of claim 1, wherein said immune response includes pro-inflammatory cytokine secretion and activation and proliferation of both CD4 and CD8 T cells.

* * * * *

```
                        SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Synthetic octapeptide from ovalbumin

<400> SEQUENCE: 1

Ser Ile Ile Asn Phe Glu Lys Leu
1               5
```